United States Patent
Sasaki et al.

(10) Patent No.: US 11,802,863 B2
(45) Date of Patent: Oct. 31, 2023

(54) OIL CONDITION DETERMINATION SYSTEM, OIL CONDITION DETERMINATION METHOD, AND OIL CONDITION DETERMINATION PROGRAM

(71) Applicant: NIPPON PILLAR PACKING CO., LTD., Osaka (JP)

(72) Inventors: Masatoshi Sasaki, Osaka (JP); Yasuteru Asakawa, Osaka (JP); Tomomi Honda, Fukui (JP); Tatsunari Koyama, Nara (JP); Akira Nakatsu, Hyogo (JP)

(73) Assignee: NIPPON PILLAR PACKING CO., LTD., Osaka (JP)

( * ) Notice: Subject to any disclaimer, the term of this patent is extended or adjusted under 35 U.S.C. 154(b) by 428 days.

(21) Appl. No.: 16/966,443

(22) PCT Filed: Jan. 30, 2019

(86) PCT No.: PCT/JP2019/003090
§ 371 (c)(1),
(2) Date: Jul. 30, 2020

(87) PCT Pub. No.: WO2019/151295
PCT Pub. Date: Aug. 8, 2019

(65) Prior Publication Data
US 2020/0363390 A1    Nov. 19, 2020

(30) Foreign Application Priority Data
Jan. 31, 2018    (JP) .................................. 2018-015699

(51) Int. Cl.
*G01N 33/28*     (2006.01)
*G01K 7/22*     (2006.01)
(Continued)

(52) U.S. Cl.
CPC .............. *G01N 33/28* (2013.01); *G01K 7/22* (2013.01); *G01N 27/06* (2013.01); *G01N 27/22* (2013.01); *G01N 27/60* (2013.01)

(58) Field of Classification Search
CPC ........ G01N 33/28; G01N 27/06; G01N 27/22; G01N 27/60; G01K 7/22
See application file for complete search history.

(56) References Cited

U.S. PATENT DOCUMENTS

2006/0232267 A1    10/2006 Halalay et al.
2008/0143351 A1*   6/2008 Lee .................... G01N 27/07
                                                 436/151
(Continued)

FOREIGN PATENT DOCUMENTS

JP    S6120848 A    1/1986
JP    2003114206 A    4/2003
(Continued)

OTHER PUBLICATIONS

International Search Report in PCT/JP2019/003090, dated Apr. 23, 2019. 4pp.

*Primary Examiner* — Amy He
(74) *Attorney, Agent, or Firm* — HAUPTMAN HAM, LLP

(57) ABSTRACT

An oil condition determination system includes a resistance value measurement unit and a determination unit. The resistance value measurement unit applies a measurement voltage between a pair of measurement electrodes in contact with oil to measure a resistance value of the oil. The determination unit determines, when a change tendency of the resistance value of the oil is reversed, that condition of the oil is changed.

17 Claims, 5 Drawing Sheets

(51) Int. Cl.
*G01N 27/06* (2006.01)
*G01N 27/22* (2006.01)
*G01N 27/60* (2006.01)

(56) References Cited

U.S. PATENT DOCUMENTS

| | | |
|---|---|---|
| 2009/0315574 A1 | 12/2009 | Akiyama et al. |
| 2010/0250156 A1 | 9/2010 | Halalay et al. |
| 2010/0300188 A1 | 12/2010 | Halalay et al. |
| 2012/0229151 A1 | 9/2012 | Katafuchi |
| 2018/0372660 A1 | 12/2018 | Yoshida et al. |

FOREIGN PATENT DOCUMENTS

| | | |
|---|---|---|
| JP | 2004176566 A | 6/2004 |
| JP | 2005337096 A | 12/2005 |
| JP | 20092693 A | 1/2009 |
| JP | 20117505 A | 1/2011 |
| WO | 2011065340 A1 | 6/2011 |
| WO | 2017187770 A1 | 11/2017 |

* cited by examiner

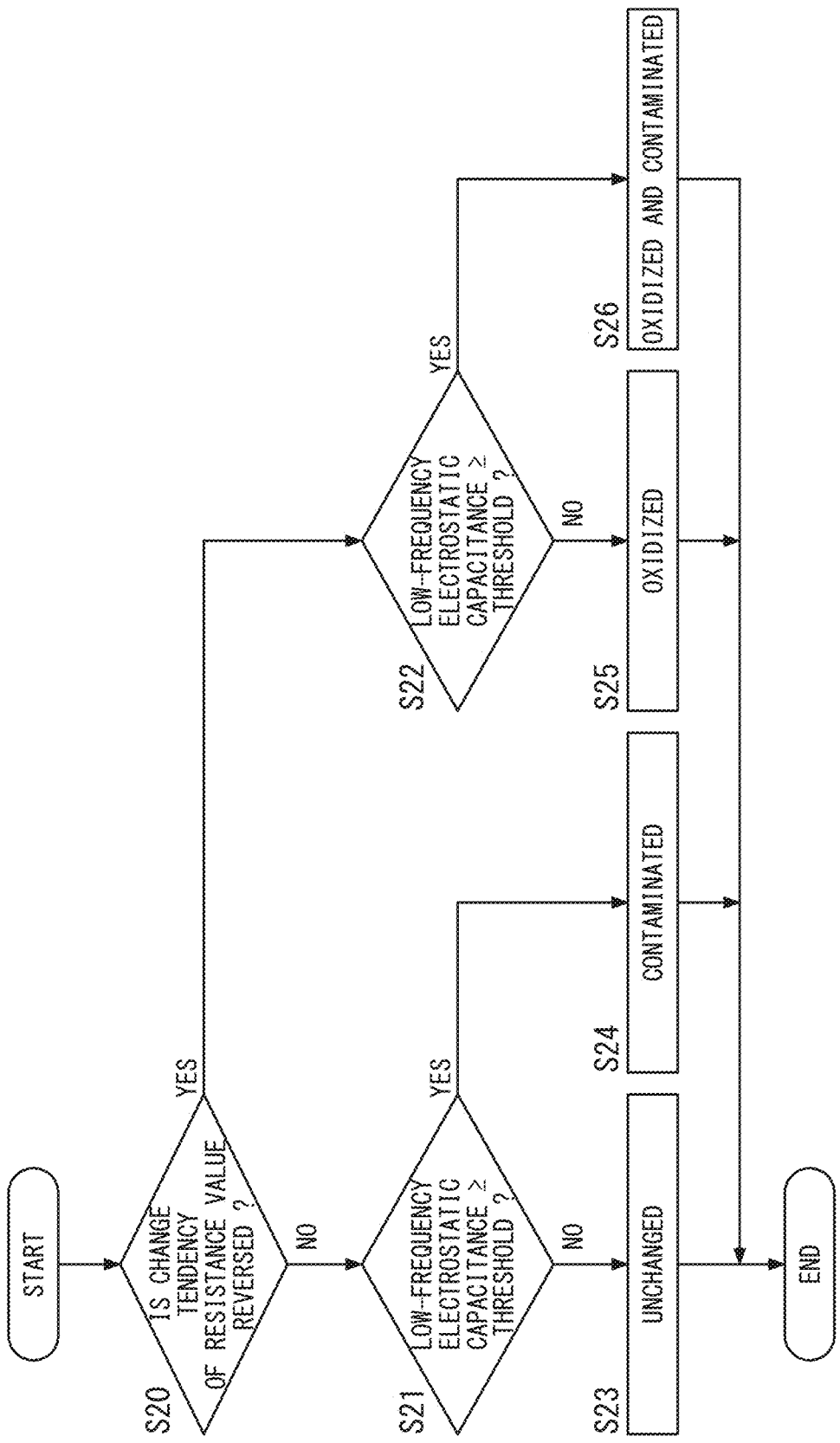

OIL CONDITION DETERMINATION SYSTEM, OIL CONDITION DETERMINATION METHOD, AND OIL CONDITION DETERMINATION PROGRAM

RELATED APPLICATIONS

The present application is a National Phase of International Application Number PCT/JP2019/003090, filed Jan. 30, 2019, and claims priority based on Japanese Patent Application No. 2018-015699, filed Jan. 31, 2018.

TECHNICAL FIELD

The present disclosure generally relates to oil condition determination systems, oil condition determination methods, and oil condition determination programs. The present disclosure specifically relates to an oil condition determination system, an oil condition determination method, and an oil condition determination program which are configured to determine whether or not condition of oil is changed.

BACKGROUND ART

Patent Literature 1 discloses an oil deterioration detection device. In the oil deterioration detection device, two polar plates are installed parallel to each other in an oil flow path, a current which flows when an alternating-current voltage is applied between the two polar plates is measured with an ammeter, and a voltage between the polar plates is measured with a voltmeter by a signal processor (process means). Then, based on measurement results by the ammeter and the voltmeter, the electric conductivity and the electrostatic capacitance of oil are obtained. Then, when either the electric conductivity or the electrostatic capacitance of the oil is a value out of the allowable range, the oil deterioration detection device determines that the oil is deteriorated.

In Patent Literature 1, the allowable range from an upper limit value to a lower limit value is set in advance for each of the electric conductivity and the electrostatic capacitance of the oil. Such an allowable range can depend on the kind of oil. Therefore, if the allowable range is not appropriately set in each case depending on the kind of oil, determination accuracy of a change in the condition of the oil may decrease.

CITATION LIST

Patent Literature

Patent Literature 1: JP 2009-2693 A

SUMMARY OF INVENTION

It is an object of the present disclosure to provide an oil condition determination system, an oil condition determination method, and an oil condition determination program which can suppress determination accuracy from being reduced due to the kind of oil.

An oil condition determination system of one aspect of the present disclosure includes: a resistance value measurement unit configured to apply a measurement voltage between a pair of measurement electrodes in contact with oil to measure a resistance value of the oil; and a determination unit configured to, when a change tendency of the resistance value of the oil is reversed, determine that condition of the oil is changed.

An oil condition determination method of one aspect of the present disclosure includes determining, when a change tendency of a resistance value of oil is reversed, that condition of the oil is changed.

An oil condition determination program of one aspect of the present disclosure is a program configured to cause one or more processors to execute the oil condition determination method.

BRIEF DESCRIPTION OF DRAWINGS

FIG. 5 is a view illustrating a remaining part of the flowchart.

DESCRIPTION OF EMBODIMENTS

1. Embodiment

1.1 Schema

Figure 1:
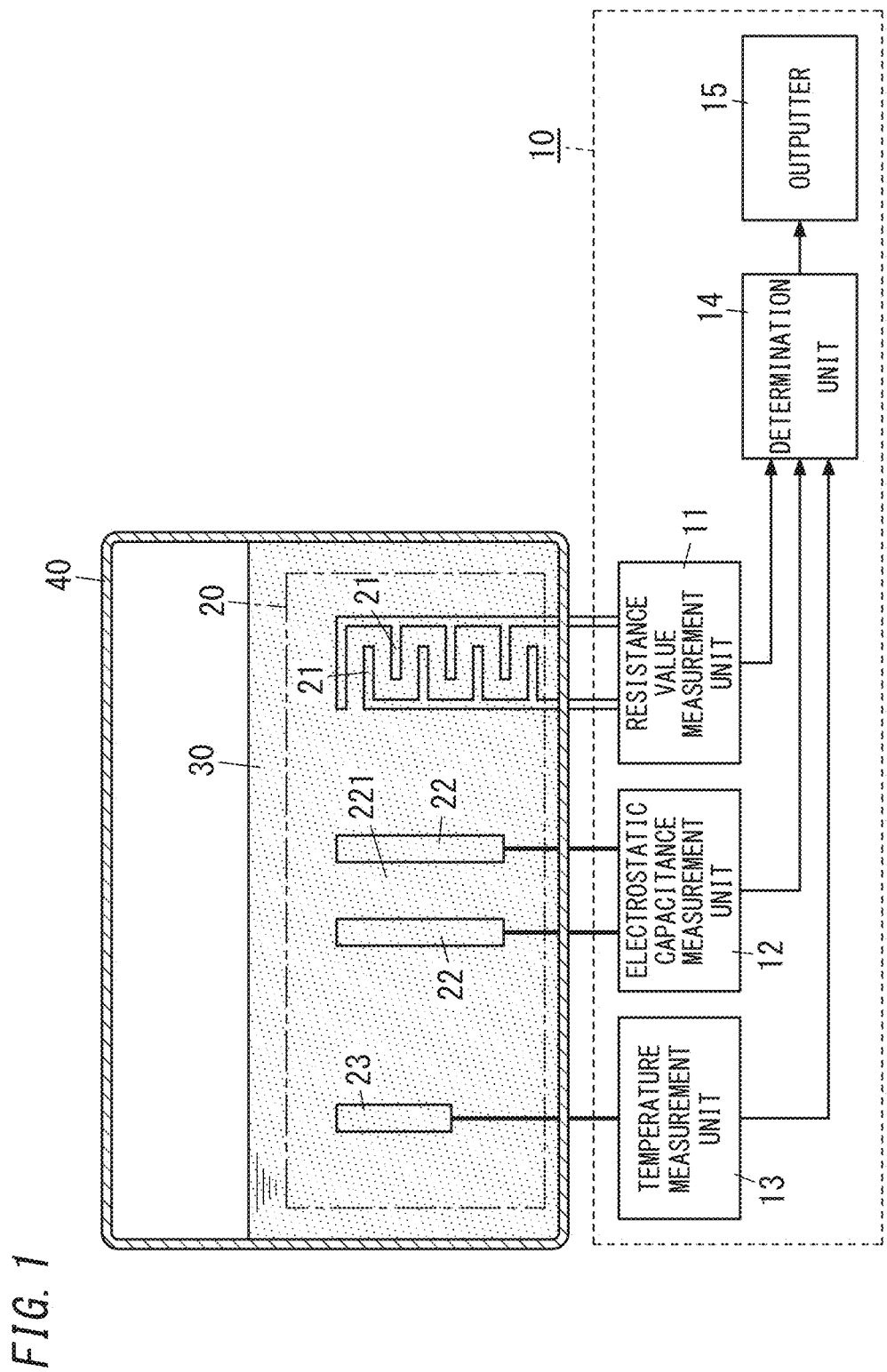
FIG. 1 is a schematic diagram illustrating an oil condition determination system of one embodiment.

FIG. 1 shows an oil condition determination system 10 of one embodiment. The oil condition determination system 10 includes a resistance value measurement unit 11 and a determination unit 14. The resistance value measurement unit 11 is configured to apply a measurement voltage between a pair of measurement electrodes 21 and 21 in contact with oil 30 to measure a resistance value of the oil 30. The determination unit 14 is configured to, when a change tendency of the resistance value of the oil 30 is reversed, determine that condition of the oil 30 is changed.

In the oil condition determination system 10, whether or not the condition of the oil 30 is changed is determined based on whether or not the change tendency of the resistance value of the oil 30 is reversed. That is, in the oil condition determination system 10, a relative value, rather than an absolute value, of the resistance value of the oil 30 is adopted. Thus, even when an initial resistance value changes depending on the kind of the oil 30, it is possible to determine whether or not the condition of the oil 30 is changed. In this way, it is possible to suppress the determination accuracy from being reduced due to the kind of the oil 30.

1.2 Configuration

The oil condition determination system 10 will be described further in detail below. The oil condition determination system 10 is a system for determining whether or not the condition of the oil 30 is changed. Here, the oil 30 is, for example, lubricating oil. In the present embodiment, the oil 30 is assumed to be engine oil used for vehicles (automobiles).

As illustrated in FIG. 1, the oil condition determination system 10 is connected to a sensor head 20. The oil condition determination system 10 determines the condition of the oil 30 based on an output from the sensor head 20.

The sensor head 20 includes the pair of measurement electrodes 21, a pair of facing electrodes 22, and a temperature sensing element 23. The pair of measurement electrodes 21 are used to measure the resistance value (impedance, in particular, reactance) of the oil 30. In the present embodiment, the pair of measurement electrodes 21 are comb-shaped electrodes. The pair of measurement electrodes 21 may be formed by, for example, patterning a conductive layer formed on one surface of a substrate into a desired shape by a lithography or etching technique. The pair of facing electrodes 22 are used to measure electrostatic capacitance resulting from the oil 30. Each of the pair of facing electrodes 22 has a rectangular plate shape. The pair of facing electrodes 22 are arranged to conform with each other in terms of their length directions, width directions, and thickness directions and to face each other in their thickness directions. In particular, the pair of facing electrodes 22 face each other with a space 221 provided therebetween. The oil 30 is to be provided in the space 221. One of the pair of facing electrodes 22 may be formed on an opposite surface of the substrate provided with the pair of measurement electrodes 21 from the pair of measurement electrodes 21. In this case, the other of the pair of facing electrodes 22 may be formed as part of a case in which the substrate is accommodated. The temperature sensing element 23 is used to measure the temperature of the oil 30. The temperature sensing element 23 is, for example, a thermistor.

The sensor head 20 having such a configuration is used in a state where the sensor head 20 is immersed in the oil 30 in an oil storage 40 as illustrated in FIG. 1. Specifically, the sensor head 20 is used in a state where part or the entirety of the sensor head 20 is immersed in the oil 30. For example, the sensor head 20 is disposed in a lower part in the oil storage 40. Thus, a state where at least part of the sensor head 20 is immersed in the oil 30 is easily achieved. In particular, the sensor head 20 is preferably disposed such that the longitudinal direction of each of the pair of facing electrodes 22 is transverse to (preferably orthogonal to) the horizontal direction. In this way, a change in the amount of the oil 30 is easily reflected on a change in the electrostatic capacitance of the oil 30 measured with the pair of facing electrodes 22. Note that in the present embodiment, the oil storage 40 is assumed to be an oil pan for engine oil.

As illustrated in FIG. 1, the oil condition determination system 10 includes the resistance value measurement unit 11, an electrostatic capacitance measurement unit 12, a temperature measurement device 13, the determination unit 14, and an outputter 15.

The resistance value measurement unit 11 is configured to apply the measurement voltage between the pair of measurement electrodes 21 in contact with the oil 30 to measure the resistance value of the oil 30. The resistance value measurement unit 11 measures the resistance value of the oil 30 at predetermined time intervals. For one measurement, the resistance value measurement unit 11 may measure the resistance value of the oil 30 a plurality of times at shorter time intervals than the predetermined time intervals. In this case, the resistance value measurement unit 11 may output an average value of a plurality of measured resistance values of the oil 30.

Specifically, the resistance value measurement unit 11 measures a current flowing between the pair of measurement electrodes 21 while applying the measurement voltage between the pair of measurement electrodes 21. The resistance value measurement unit 11 obtains a resistance value (impedance) between the pair of measurement electrodes 21 from the current measured. When the pair of measurement electrodes 21 are entirely in contact with the oil 30, the resistance value between the pair of measurement electrodes 21 may be regarded as the resistance value of the oil 30. In the present embodiment, the measurement voltage is an alternating-current voltage. Note that the measurement voltage does not necessarily have to be an alternating-current voltage but may be a direct-current voltage. However, even when the measurement voltage is a direct-current voltage, the direct-current voltage is preferably a voltage varying with time.

The electrostatic capacitance measurement unit 12 is configured to apply an alternating-current voltage at a prescribed frequency between the pair of facing electrodes 22 to measure the electrostatic capacitance between the pair of facing electrodes 22. The pair of facing electrodes 22 face each other with the space 221 provided therebetween. The oil 30 is to be provided in the space 221. The electrostatic capacitance measurement unit 12 measures the electrostatic capacitance at predetermined time intervals. For one measurement, the electrostatic capacitance measurement unit 12 may measure the electrostatic capacitance a plurality of times at shorter time intervals than the predetermined time intervals. In this case, the electrostatic capacitance measurement unit 12 may output an average value of a plurality of measured electrostatic capacitances.

When the space 221 is filled with the oil 30, the electrostatic capacitance between the pair of facing electrodes 22 is mainly influenced by the permittivity of the oil 30. In contrast, when the space 221 is not filled with the oil 30, the electrostatic capacitance between the pair of facing electrodes 22 is mainly influenced by mainly the occupancy of the oil 30 in the space 221. Thus, it is possible to determine the permittivity of the oil 30 and the amount of the oil 30 based on the electrostatic capacitance between the pair of facing electrodes 22. In the present embodiment, the electrostatic capacitance measurement unit 12 is configured to switch the prescribed frequency between a first frequency and a second frequency higher than the first frequency. In a comparison between an alternating-current voltage at the first frequency and an alternating-current voltage at the second frequency, the alternating-current voltage at the first frequency corresponds to a low frequency, and the alternating-current voltage at the second frequency corresponds to a high frequency. The first frequency is a frequency for determination of the permittivity of the oil 30. On the other hand, the second frequency is a frequency for determination of the amount of the oil 30. The first frequency and the second frequency depend on the permittivity of the oil 30 and respectively have, for example, a value within a range of 100 Hz to 1 kHz and a value within a range of 10 kHz to 100 kHz. In the following description, as necessary, electrostatic capacitance measured by applying the alternating-current voltage at the first frequency between the pair of facing electrodes 22 is referred to as low-frequency electrostatic capacitance, and electrostatic capacitance measured by applying the alternating-current voltage at the second frequency between the pair of facing electrodes 22 is referred to as high-frequency electrostatic capacitance.

The temperature measurement device 13 is configured to measure the temperature of the oil 30. Specifically, the temperature measurement device 13 measures the temperature of the oil 30 based on an output from the temperature sensing element 23. The temperature measurement device 13 measures the temperature of the oil 30 at predetermined time intervals. For one measurement, the temperature measurement device 13 may measure the temperature of the oil 30 a plurality of times at shorter time intervals than the predetermined time intervals. In this case, the temperature measurement device 13 may output an average value of a plurality of measured temperatures of the oil 30.

Figure 2:
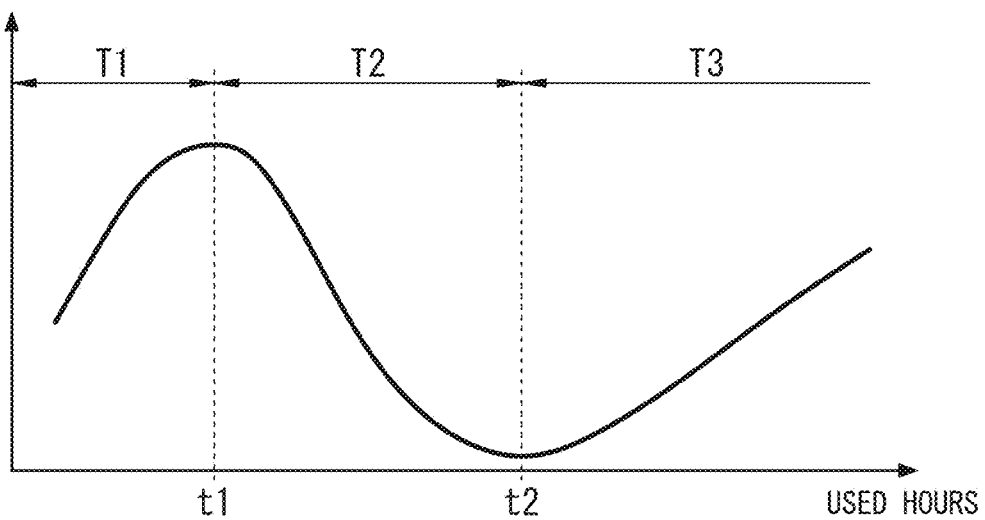
FIG. 2 is a graph illustrating time variation of electric conductivity of oil.

The determination unit 14 receives the resistance value of the oil 30 from the resistance value measurement unit 11 and stores the resistance value. Thus, the determination unit 14 stores time-series data of the resistance value of the oil 30. The determination unit 14 is configured to determine, based on the time-series data of the resistance value of the oil 30, a change in the condition of the oil 30. Here, the inventors of the present application conducted studies and found a correlation relationship between the resistance value and used hours of the oil 30 as illustrated in FIG. 2. Here, the used hours are hours for which the oil 30 is actually used. In the example of the engine oil, the used hours correspond to hours for which a vehicle is driven by an engine. According to the correlation relationship between the resistance value and the used hours of the oil 30, the change tendency of the resistance value of the oil 30 changes from an increasing tendency to a decreasing tendency at time point t1 and changes from the decreasing tendency to the increasing tendency at time point t2. An increase of the resistance value of the oil 30 until the time point t1 results from consumption (decrease) of an additive contained in the oil 30. A decrease of the resistance value of the oil 30 from the time point t1 to the time point t2 results from oxidation of the oil 30 (increased oxidized products). An increase of the resistance value of the oil 30 after the time point t2 results from an increase of sludge. As described above, the change in the resistance value of the oil 30 is classified into phase T1 in which the additive in the oil 30 is consumed, phase T2 in which the oil 30 is oxidized, and phase T3 in which sludge in the oil 30 increases. Between the phases, the change tendency of the resistance value of the oil 30 is reversed. Thus, it is possible to determine whether or not the condition of the oil 30 is changed based on whether or not the change tendency of the resistance value of the oil 30 is reversed.

From the above points, the determination unit 14 is configured to, when the change tendency of the resistance value of the oil 30 is reversed, determine that condition of the oil 30 is changed. In particular, in the present embodiment, the determination unit 14 determines, when the change tendency of the resistance value of the oil 30 changes from the decreasing tendency to the increasing tendency, that oxidation of the oil 30 occurs. Here, the determination unit 14 is configured to determine the change tendency of the resistance value of the oil 30 based on a difference between the resistance value of the oil 30 at a first time point and the resistance value of the oil 30 at a second time point next to the first time point. The difference between the resistance value of the oil 30 at the first time point and the resistance value of the oil 30 at the second time point next to the first time point is a difference between resistance values of the oil 30 at adjacent time points in the time-series data of the resistance value of the oil 30. The difference is, for example, a value obtained by subtracting a previous resistance value of the oil 30 from a current resistance value of the oil 30. Thus, a positive difference means that the resistance value of the oil 30 has increased, and a negative difference means that the resistance value of the oil 30 has decreased. In this way, it is possible to improve the determination accuracy of the change in the condition of the oil 30. Moreover, the determination unit 14 is configured to, when the resistance value of the oil 30 changes in the same direction (positive direction or negative direction) consecutively a prescribed number of times, determine the change tendency of the resistance value of the oil 30. For example, when the difference is positive the prescribed number of times consecutively, the determination unit 14 determines that the change tendency of the resistance value of the oil 30 is the increasing tendency. In contrast, when the difference is negative the prescribed number of times consecutively, the determination unit 14 determines that the change tendency of the resistance value of the oil 30 is the decreasing tendency. This enables influence of noise or the like to be eliminated or reduced and the change tendency of the resistance value of the oil 30 to be more accurately determined. Note that the prescribed number of times is not particularly limited but may be, for example, three to five times.

Moreover, the determination unit 14 receives electrostatic capacitances (low-frequency electrostatic capacitance and high-frequency electrostatic capacitance) between the pair of facing electrodes 22 from the electrostatic capacitance measurement unit 12 and stores the electrostatic capacitances. In this way, the determination unit 14 stores time-series data of the electrostatic capacitances (low-frequency electrostatic capacitance and high-frequency electrostatic capacitance) between the pair of facing electrodes 22. The determination unit 14 is configured to determine, based on the time-series data of the electrostatic capacitances between the pair of facing electrodes 22, the change in the condition and the amount of the oil 30.

Moreover, the determination unit 14 is configured to, when the electrostatic capacitance of the oil 30 is greater than or equal to a threshold, determine that the condition of the oil 30 is changed. In the present embodiment, the electrostatic capacitance measurement unit 12 measures the low-frequency electrostatic capacitance and the high-frequency electrostatic capacitance. The determination unit 14 is configured to, when the low-frequency electrostatic capacitance (electrostatic capacitance corresponding to the first frequency) is greater than or equal to the threshold, determine that the condition of the oil 30 is changed. This enables the condition of the oil 30 to be more accurately determined. In particular, the electrostatic capacitance of the oil 30 increases as impurities contained in the oil 30 increase. Examples of the impurities include moisture and soot. Thus, when the electrostatic capacitance of the oil 30 is greater than or equal to the threshold, the oil 30 may be contaminated. Note that the threshold may be determined by, for example, actually measuring the electrostatic capacitance of the oil 30 contaminated.

Moreover, the determination unit 14 is configured to, when the electrostatic capacitance of the oil 30 is greater than or equal to a determination value, determine that the amount of the oil 30 is changed. In the present embodiment, the electrostatic capacitance measurement unit 12 measures the low-frequency electrostatic capacitance and the high-frequency electrostatic capacitance. The determination unit 14 is configured to, when the high-frequency electrostatic capacitance (electrostatic capacitance corresponding to the second frequency) is greater than or equal to the threshold, determine that the amount of the oil 30 is changed. Thus, it is possible to determine, based on the change in the amount (level of liquid) of the oil 30, whether or not addition of oil 30 is performed. Specifically, the determination unit 14 obtains a difference between a current high-frequency electrostatic capacitance of the oil 30 and a previous high-frequency electrostatic capacitance of the oil 30, and when the difference obtained is greater than or equal to the determination value, the determination unit 14 determines that the amount of the oil 30 is changed. Naturally, the addition of the oil 30 is performed in the case of running short of the oil 30 and is thus performed when the occupancy of the oil 30 in the space 221 decreases. When the addition of the oil 30 is performed, the occupancy is expected to be 100%. Therefore, the addition of the oil 30 may significantly change the high-frequency electrostatic capacitance. Note that the determination value may be determined based on, for example, a change amount of the high-frequency electrostatic capacitance of the oil 30 when the addition of the oil 30 is actually performed.

Figure 3:
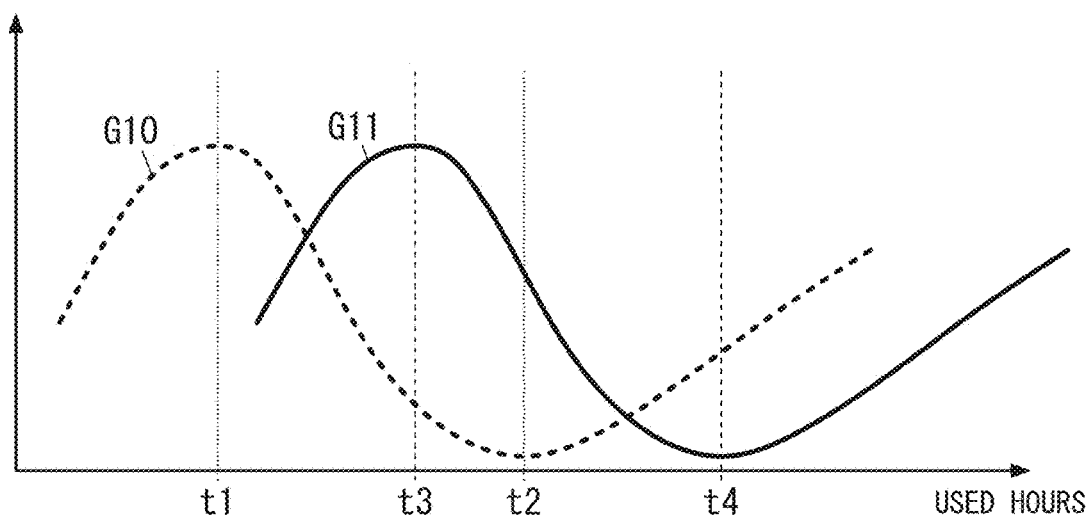
FIG. 3 is a graph illustrating time variation of the electric conductivity of the oil, in particular, when addition of oil is performed.

Here, the determination unit 14 is configured such that when the determination unit 14 determines that the amount of the oil 30 is changed, the determination unit 14 refrains from using, for determination of whether or not the condition of the oil 30 is changed, a resistance value of the oil 30 before determining that the amount of the oil 30 is changed. This enables a reduction in erroneous determination resulting from the change in the resistance value of the oil 30 before and after the addition of the oil 30. Specifically, when the determination unit 14 determines that the amount of the oil 30 is changed, the determination unit 14 initializes the time-series data of the resistance value of the oil 30. This is because the addition of the oil 30 significantly changes the correlation relationship between the resistance value and the used hours of the oil 30. For example, in FIG. 3, graph G10 shows a correlation relationship between the resistance value and the used hours of the oil 30 before the addition of the oil 30, and graph G11 shows a correlation relationship between the resistance value and the used hours of the oil 30 after the addition of the oil 30. As can be clearly seen from FIG. 3, the graph G10 shows that the change in the resistance value changes from the increasing tendency to the decreasing tendency at the time point t1, and the graph G11 shows that the change in the resistance value changes from the increasing tendency to the decreasing tendency at time point t3 later than the time point t1. Moreover, the graph G10 shows that the change in the resistance value changes from the decreasing tendency to the increasing tendency at the time point t2, and the graph G11 shows that the change in the resistance value changes from the decreasing tendency to the increasing tendency at time point t4 later than the time point t2. Note that in FIG. 3, to make the description easy to understand, the graph G11 corresponds to a graph obtained by parallelly moving the graph G10 along an axis representing the used hours, but actually, the graph G11 may be a more complicated graph depending on the amount of added oil 30.

As described above, when the low-frequency electrostatic capacitance (electrostatic capacitance corresponding to the first frequency) is greater than or equal to the threshold, the determination unit 14 determines that the condition of the oil 30 is changed. When the high-frequency electrostatic capacitance (electrostatic capacitance corresponding to the second frequency) is greater than or equal to the threshold, the determination unit 14 determines that the amount of the oil 30 is changed. This enables the determination accuracy of the change in the amount of the oil 30 and the change in the condition of the oil 30 to be improved while the pair of facing electrodes 22 are used to determine both the change in the amount of the oil 30 and the change in the condition of the oil 30.

The determination unit 14 receives the temperature of the oil 30 from the temperature measurement device 13 and stores the temperature. Thus, the determination unit 14 stores time-series data of the temperature of the oil 30. Here, the resistance value and the electrostatic capacitance of the oil 30 between the pair of facing electrodes 22 are influenced by the temperature of the oil 30. Thus, measurement results of the resistance value and the electrostatic capacitance may involve errors depending on the temperature of the oil 30. Therefore, the determination unit 14 corrects the resistance value and the electrostatic capacitance in accordance with the temperature of the oil 30 obtained from the temperature measurement device 13. That is, the determination unit 14 is configured to perform temperature compensation of the resistance value and the electrostatic capacitance of the oil 30 between the pair of facing electrodes 22 based on the temperature of the oil 30 measured by the temperature measurement device 13. The temperature compensation of the resistance value of the oil 30 may be performed with reference to a mathematical formula or table prepared based on the correlation relationship of the temperature and the resistance value of the oil 30. Similarly, the temperature compensation of the electrostatic capacitance between the pair of facing electrodes 22 may be performed with reference to a mathematical formula or table prepared based on the correlation relationship between the electrostatic capacitance between the pair of facing electrodes 22 and the temperature. In this way, it is possible to improve the determination accuracy of the change in the condition of the oil 30.

In the present embodiment, the oil 30 is engine oil, and the temperature of the engine oil is often higher than or equal to 60° C. while the vehicle is running. The change in the condition of the oil 30 may be caused due to an increase in the running time of the vehicle, that is, an increase in used hours of the oil 30. In other words, when the oil 30 is not used, the necessity of determining the change in the condition of the oil 30 by the determination unit 14 is low. Therefore, in the present embodiment, the determination unit 14 is configured to, when the temperature of the oil 30 is higher than or equal to a prescribed start temperature (e.g., 60° C.), determine the change in the condition of the oil 30. This enables electric power consumption by the determination unit 14 to be reduced.

The determination unit 14 described above is, for example, realized by one or more processors (microprocessors) and one or more memory elements. That is, the determination unit 14 is realized by a program (oil condition determination program) executed by the one or more processors. When the oil condition determination program is executed by the one or more processors, the oil condition determination program causes the one or more processor to execute an oil condition determination method. The oil condition determination method includes determining, when the change tendency of the resistance value of the oil 30 is reversed, that the condition of the oil 30 is changed. According to the oil condition determination program and the oil condition determination method as described above, it is possible to suppress the determination accuracy from being reduced due to the kind of the oil 30 in a similar manner to the oil condition determination system 10. The oil condition determination program may be stored in the memory in advance, provided via a telecommunications network such as the Internet, or provided by a non-transitory storage medium such as a memory card storing the program.

The outputter 15 is configured to output a determination result by the determination unit 14. Thus, it is possible to output the change in the condition of the oil 30. The outputter 15 is a communication interface configured to output the determination result by the determination unit 14 to an external device based on a prescribed communication scheme. The communication scheme of the outputter 15 may be a wired or wireless system.

1.3 Operation

Figure 4:
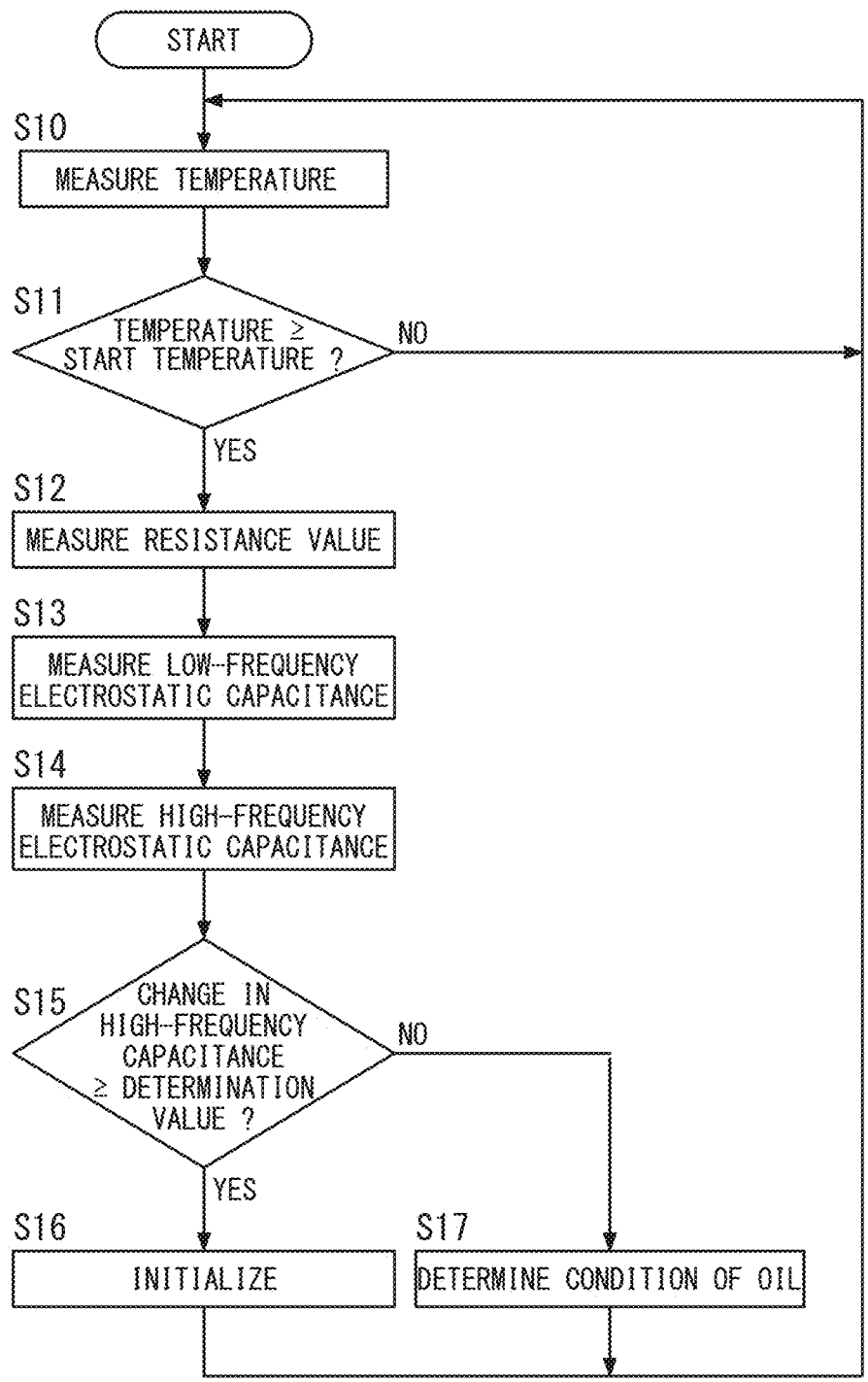
FIG. 4 is a view illustrating part of a flowchart of operation of the oil condition determination system.

With reference to flowcharts in FIGS. 4 and 5, operation of the oil condition determination system 10 will be briefly described below. The oil condition determination system 10 starts operating, for example, when the engine of the vehicle is started and an acceleration sensor of the vehicle senses that the vehicle starts moving.

First, the oil condition determination system 10 measures the temperature of the oil 30 by the temperature measurement device 13 (S10). Then, the determination unit 14 determines whether or not the temperature measured by the temperature measurement device 13 is higher than or equal to a start temperature (S11). If the temperature measured by the temperature measurement device 13 is lower than the start temperature (S11: NO), the process returns to step S10. In contrast, if the temperature measured by the temperature measurement device 13 is higher than or equal to the start temperature (S11: YES), the resistance value measurement unit 11 measures the resistance value of the oil 30 (S12), and the electrostatic capacitance measurement unit 12 measures the low-frequency electrostatic capacitance and the high-frequency electrostatic capacitance (S13, S14). Thereafter, the determination unit 14 determines whether or not the change in the high-frequency electrostatic capacitance is greater than or equal to the determination value (S15). If the change in the high-frequency electrostatic capacitance is greater than or equal to the determination value, the determination unit 14 initializes the time-series data of the resistance value of the oil 30 (S16). Then, the process returns to step S10. Thus, when addition of oil 30 is performed, previous time-series data of the resistance value of the oil 30 is discarded, and time-series data of the resistance value of the oil 30 is newly stored. In contrast, if the change in the high-frequency electrostatic capacitance is greater than or equal to the determination value, the determination unit 14 performs a process of determining the condition of the oil 30 (S17).

Next, with reference to a flowchart in FIG. 5, the process of determining the condition of the oil 30 (S17) will be described. First, the determination unit 14 determines whether or not the change tendency of the resistance value of the oil 30 is reversed (S20). In the present embodiment, the determination unit 14 determines whether or not the change tendency of the resistance value of the oil 30 changes from the decreasing tendency to the increasing tendency. Here, if the change tendency of the resistance value of the oil 30 does not change from the decreasing tendency to the increasing tendency (S20: NO), the determination unit 14 determines whether or not the low-frequency electrostatic capacitance is greater than or equal to the threshold (S21). In contrast, if the change tendency of the resistance value of the oil 30 changes from the decreasing tendency to the increasing tendency (S20: YES), the determination unit 14 determines whether or not the low-frequency electrostatic capacitance is greater than or equal to the threshold (S22). Here, in step S21, if the low-frequency electrostatic capacitance is not greater than or equal to the threshold (S21: NO), the determination unit 14 determines that the condition of the oil 30 is not changed from the initial state (that is, no defect is found), and the determination unit 14 outputs the determination result to the outputter 15 (S23). In step S21, if the low-frequency electrostatic capacitance is greater than or equal to the threshold (S21: YES), the determination unit 14 determines that the oil 30 is not oxidized but is contaminated, and the determination unit 14 outputs the determination result to the outputter 15 (S24). In step S22, if the low-frequency electrostatic capacitance is not greater than or equal to the threshold (S22: NO), the determination unit 14 determines that the oil 30 is oxidized but is not contaminated, and the determination unit 14 outputs the determination result to the outputter 15 (S25). In step S22, if the low-frequency electrostatic capacitance is greater than or equal to the threshold (S22: YES), the determination unit 14 determines that the oil 30 is oxidized and is contaminated, and the determination unit 14 outputs the determination result to the outputter 15 (S26).

The determination results by the oil condition determination system 10 may be displayed on, for example, an indicator panel of the vehicle. In each case of steps S24, S25, and S26, notification of a change in the condition of the oil 30 is given. Such notification can inform a user of arrival of time to change the oil 30.

2. Variation

The above-described embodiment is a mere example of various embodiments of the present disclosure. Various modifications may be made to the above-described embodiment depending on design and the like as long as the object of the present disclosure can be achieved. Variations of the embodiment will be described below.

For example, in the above-described embodiment, the oil 30 is engine oil of a vehicle, but the oil condition determination system 10 is applicable to oil other than the engine oil of the vehicle. For example, the oil condition determination system 10 is applicable to lubricating oil of, for example, a facility apparatus.

For the determination of the condition of the oil 30 and the determination of the amount of the oil 30, the same facing electrodes 22 are used in the above-described embodiment, but different facing electrodes may be prepared. The condition of the oil 30 and the amount of the oil 30 may be determined based on electrostatic capacitance obtained by applying the same alternating-current voltage to the same facing electrodes 22.

The determination unit 14 may determine, by an operation from the time-series data of the resistance value of the oil 30, whether or not the change tendency of the resistance value of the oil 30 is reversed. For example, a differential operation may be performed on the time-series data of the resistance value of the oil 30 to extract an inflection point.

In the above-described oil condition determination system 10, the determination unit 14 is essential, but other components may not be necessarily needed.

For example, the oil condition determination system 10 does not have to include the electrostatic capacitance measurement unit 12. That is, the determination unit 14 does not necessarily have to determine, based on the electrostatic capacitance, whether or not the condition of the oil 30 is changed. Moreover, the determination unit 14 does not have to determine, based on the change in the electrostatic capacitance, whether or not the amount of the oil 30 is changed. For example, unlike a 2-stroke engine, a 4-stroke engine generally does not consume engine oil, and therefore, the engine oil is changed but addition of oil is not performed. In such a case, the necessity of determining the change in the amount of the oil 30 by the determination unit 14 is low.

For example, the oil condition determination system 10 does not have to include the temperature measurement device 13. That is, the determination unit 14 does not necessarily have to perform temperature compensation of the resistance value of the oil 30 based on the temperature. In particular, when the temperature dependency of the resistance value of the oil 30 is relatively low, the temperature compensation may not necessarily have to be performed.

3. Aspects

As can be clearly seen from the embodiment and variations described above, an oil condition determination system (10) of a first aspect includes a resistance value measurement unit (11) and a determination unit (14). The resistance value measurement unit (11) is configured to apply a measurement voltage between a pair of measurement electrodes (21) in contact with oil (30) to measure a resistance value of the oil (30). The determination unit (14) is configured to, when a change tendency of the resistance value of the oil (30) is reversed, determine that condition of the oil (30) is changed. The first aspect enables the determination accuracy to be suppressed from being reduced due to the kind of the oil (30).

An oil condition determination system (10) of a second aspect would be realized in combination with the first aspect. In the second aspect, the determination unit (14) is configured to determine the change tendency of the resistance value of the oil (30) based on a difference between a resistance value of the oil (30) at a first time point and a resistance value of the oil (30) at a second time point next to the first time point. The second aspect enables the determination accuracy of the change in the condition of the oil (30) to be improved.

An oil condition determination system (10) of a third aspect would be realized in combination with the first or second aspect. In the third aspect, the determination unit (14) is configured to determine, when the resistance value of the oil (30) changes in a same direction a prescribed number of times consecutively, the change tendency of the resistance value of the oil (30). The third aspect enables the change tendency of the resistance value of the oil (30) to be more accurately determined.

An oil condition determination system (10) of a fourth aspect can be realized in combination of any one of the first to third aspects. In the fourth aspect, the determination unit (14) is configured to, when the change tendency of the resistance value of the oil (30) is reversed, determine that the oil (30) is oxidized. The fourth aspect enables determination of whether or not the oil (30) is oxidized.

An oil condition determination system (10) of a fifth aspect can be realized in combination of any one of the first to fourth aspects. With the fifth aspect, the measurement voltage is an alternating-current voltage. The fifth aspect enables the measurement accuracy of the resistance value of the oil to be improved.

An oil condition determination system (10) of a sixth aspect can be realized in combination of any one of the first to fifth aspects. In the sixth aspect, the oil condition determination system (10) further includes an electrostatic capacitance measurement unit (12). The electrostatic capacitance measurement unit (12) is configured to apply an alternating-current voltage at a prescribed frequency between a pair of facing electrodes (22) to measure electrostatic capacitance between the pair of facing electrodes (22). The pair of facing electrodes (22) face each other with a space (221) provided therebetween. The oil (30) is to be provided in the space (221). The determination unit (14) is configured to, when the electrostatic capacitance is greater than or equal to a threshold, determine that the condition of the oil (30) is changed. The sixth aspect enables the condition of the oil (30) to be more accurately determined.

An oil condition determination system (10) of a seventh aspect would be realized in combination with the sixth aspect. In the seventh aspect, the determination unit (14) is configured to, when the electrostatic capacitance is greater than or equal to the threshold, determine that the oil (30) is contaminated. The seventh aspect enables determination of whether or not the oil (30) is contaminated.

An oil condition determination system (10) of an eighth aspect would be realized in combination with the sixth or seventh aspect. In the eighth aspect, the determination unit (14) is configured to, when a change in the electrostatic capacitance is greater than or equal to a determination value, determine that an amount of the oil (30) is changed. The eighth aspect enables determination, based on the change in the amount (level of liquid) of the oil 30, whether or not addition of oil 30 is performed.

An oil condition determination system (10) of a ninth aspect would be realized in combination with the eighth aspect. In the ninth aspect, the determination unit (14) is configured such that when the determination unit (14) determines that the amount of the oil (30) is changed, the determination unit (14) refrains from using, for determination of whether or not the condition of the oil (30) is changed, a resistance value of the oil (30) before determining that the amount of the oil (30) is changed. The ninth aspect enables a reduction in erroneous determination resulting from the change of the resistance value of the oil (30) before and after the addition of the oil (30).

An oil condition determination system (10) of a tenth aspect would be realized in combination with any one of the sixth to ninth aspects. In the tenth aspect, the electrostatic capacitance measurement unit (12) is configured to switch the prescribed frequency between a first frequency and a second frequency higher than the first frequency. The determination unit (14) is configured to, when the electrostatic capacitance corresponding to the first frequency is greater than or equal to a threshold, determine that the condition of the oil (30) is changed. The determination unit (14) is configured to, when a change in the electrostatic capacitance corresponding to the second frequency is greater than or equal to a determination value, determine that an amount of the oil (30) is changed. The tenth aspect enables the determination accuracy of the change in the amount of the oil (30) and the change in the condition of the oil (30) to be improved while the pair of facing electrodes (22) are used to determine both the change in the amount of the oil (30) and the change in the condition of the oil (30).

An oil condition determination system (10) of an eleventh aspect would be realized in combination with any one of the first to tenth aspects. In the eleventh aspect, the oil condition determination system (10) further includes a temperature measurement device (13) configured to measure temperature of the oil (30). The determination unit (14) is configured to perform temperature compensation of the resistance value of the oil (30) based on the temperature of the oil (30) measured by the temperature measurement device (13). The eleventh aspect enables the determination accuracy of the change in the condition of the oil (30) to be improved.

An oil condition determination system (10) of a twelfth aspect would be realized in combination with any one of the first to eleventh aspects. In the twelfth aspect, the oil condition determination system (10) further includes a temperature measurement device (13) configured to measure temperature of the oil (30). The determination unit (14) is configured to, when the temperature of the oil (30) measured by the temperature measurement device (13) is higher than or equal to a prescribed start temperature, determine a change in the condition of the oil (30). The twelfth aspect enables electric power consumption by the determination unit (14) to be reduced.

An oil condition determination system (10) of a thirteenth aspect would be realized in combination with any one of the first to twelfth aspects. In the thirteenth aspect, the oil condition determination system (10) further includes an outputter (15) configured to output a determination result by the determination unit (14). The thirteenth aspect enables the change in the condition of the oil (30) to be output.

An oil condition determination method of a fourteenth aspect includes determining, when the change tendency of the resistance value of the oil (30) is reversed, that the condition of the oil (30) is changed. The fourteenth aspect enables the determination accuracy to be suppressed from being reduced due to the kind of the oil (30).

An oil condition determination program of a fifteenth aspect is a program configured to cause one or more processors to execute the oil condition determination method of the fourteenth aspect. The fifteenth aspect enables the determination accuracy to be suppressed from being reduced due to the kind of the oil (30).

REFERENCE SIGNS LIST

10 OIL CONDITION DETERMINATION SYSTEM
11 RESISTANCE VALUE MEASUREMENT UNIT
12 ELECTROSTATIC CAPACITANCE MEASUREMENT UNIT
13 TEMPERATURE MEASUREMENT UNIT
14 DETERMINATION UNIT
15 OUTPUTTER
21 MEASUREMENT ELECTRODE
22 FACING ELECTRODE
30 OIL

The invention claimed is:

1. An oil condition determination system, comprising:
a resistance value measurement unit configured to apply a measurement voltage between
a pair of measurement electrodes in contact with oil to measure a resistance value of the oil; and
a determination unit configured to, when a change tendency of the resistance value of the oil is reversed, determine that condition of the oil is changed, wherein
a change in the resistance value of the oil has
a first phase in which an additive in the oil is consumed,
a second phase in which an oxidized product in the oil increases, and
a third phase in which sludge in the oil increases,
the determination unit is configured to determine, when the change tendency of the resistance value of the oil between the second phase to the third phase changes from a decreasing tendency to an increasing tendency, that a condition of oxidation of the oil is changed.

2. The oil condition determination system of claim 1, wherein
the determination unit is configured to determine the change tendency of the resistance value of the oil based on a difference between a resistance value of the oil at a first time point and a resistance value of the oil at a second time point next to the first time point.

3. The oil condition determination system of claim 1, wherein
the determination unit is configured to, when the resistance value of the oil changes in a same direction a prescribed number of times consecutively, determine the change tendency of the resistance value of the oil.

4. The oil condition determination system of claim 1, wherein
the determination unit is configured to, when the change tendency of the resistance value of the oil is reversed, determine that the oil is oxidized.

5. The oil condition determination system of claim 1, wherein
the measurement voltage is an alternating-current voltage.

6. The oil condition determination system of claim 1, further comprising:
an electrostatic capacitance measurement unit configured to apply an alternating-current voltage at a prescribed frequency between a pair of facing electrodes to measure electrostatic capacitance between the pair of facing electrodes, the pair of facing electrodes facing each other with a space provided therebetween, the oil being provided in the space, wherein
the determination unit is configured to, when the electrostatic capacitance is greater than or equal to a threshold, determine that the condition of the oil is changed.

7. The oil condition determination system of claim 6, wherein
the determination unit is configured to, when the electrostatic capacitance is greater than or equal to the threshold, determine that the oil is contaminated.

8. The oil condition determination system of claim 6, wherein
the determination unit is configured to, when a change in the electrostatic capacitance is greater than or equal to a determination value, determine that an amount of the oil is changed.

9. The oil condition determination system of claim 8, wherein
the determination unit is configured such that when the determination unit determines that the amount of the oil is changed, the determination unit refrains from using, for determination of whether or not the condition of the oil is changed, a resistance value of the oil before determining that the amount of the oil is changed.

10. The oil condition determination system of claim 1, further comprising:
a temperature measurement device configured to measure temperature of the oil, wherein
the determination unit is configured to perform temperature compensation of the resistance value of the oil based on the temperature of the oil measured by the temperature measurement device.

11. The oil condition determination system of claim 1, further comprising:
a temperature measurement device configured to measure temperature of the oil, wherein
the determination unit is configured to, when the temperature of the oil measured by the temperature measurement device is higher than or equal to a prescribed start temperature, determine a change in the condition of the oil.

12. The oil condition determination system of claim 1, further comprising:
an output configured to output a determination result by the determination unit.

13. An oil condition determination system, comprising
a resistance value measurement unit configured to apply a measurement voltage between a pair of measurement electrodes in contact with oil to measure a resistance value of the oil;
a determination unit configured to, when a change tendency of the resistance value of the oil is reversed, determine that condition of the oil is changed; and
an electrostatic capacitance measurement unit configured to apply an alternating-current voltage at a prescribed frequency between a pair of facing electrodes to measure electrostatic capacitance between the pair of facing electrodes, the pair of facing electrodes facing each other with a space provided therebetween, the oil being to be provided in the space, wherein the electrostatic capacitance measurement unit is configured to switch the prescribed frequency between a first frequency and a second frequency higher than the first frequency, the determination unit is configured to, when the electrostatic capacitance corresponding to the first frequency is greater than or equal to a threshold, determine that the condition of the oil is changed, and the determination unit is configured to, when a change in the electrostatic capacitance corresponding to the second frequency is greater than or equal to a determination value, determine that an amount of the oil is changed.

14. An oil condition determination method, comprising:

determining, when a change tendency of a resistance value of oil is reversed, that condition of the oil is changed, wherein a change of the resistance value of the oil has
 a first phase in which an addictive in the oil is consumed,
 a second phase in which an oxidized product in the oil increases, and
 a third phase in which sludge in the oil increases, in the step for determining that the condition of the oil changes, determining, when the change tendency of the resistance value of the oil between the second phase to the third phase changes from a decreasing tendency to an increasing tendency, that a condition of oxidation of the oil is changed.

15. A non-transitory computer readable medium storing an oil condition determination program configured to cause one or more processor to execute the oil condition determination method of claim 14.

16. An oil condition determination system of claim 1, comprising:

a resistance value measurement unit configured to apply a measurement voltage between a pair of measurement electrodes in contact with oil to measure a resistance value of the oil; and a determination unit configured to, when a change tendency of the resistance value of the oil is reversed, determine that condition of the oil is changed, wherein the determination unit is configured to determine, when the change tendency of the resistance value of the oil changes from a decreasing tendency to an increasing tendency, that oxidation of the oil occurs.

17. An oil condition determination system, comprising:

a resistance value measurement unit configured to apply a measurement voltage between a pair of measurement electrodes in contact with oil to measure a resistance value of the oil; and a determination unit configured to, when a change tendency of the resistance value of the oil is reversed, determine that condition of the oil is changed, wherein a change of the resistance value of the oil has
 a first phase in which an addictive in the oil is consumed,
 a second phase in which an oxidized product in the oil increases, and
 a third phase in which sludge in the oil increases, the change tendency of the resistance value of the oil changes between the first phase and the second phase and between the second phase and the third phase, the determination unit is configured to determine,
 when the change tendency of the resistance value of the oil between the first phase and the second phase changes from an increasing tendency to a decreasing tendency, that an addictive in the oil is consumed, and
 when a change tendency between the second phase and the third phase changes from a decreasing tendency to an increasing tendency, that oxidation of the oil occurs.

* * * * *